(12) United States Patent
Hartley et al.

(10) Patent No.: US 8,753,385 B2
(45) Date of Patent: Jun. 17, 2014

(54) PRELOADED STENT GRAFT DELIVERY DEVICE

(75) Inventors: David Ernest Hartley, Wannanup (AU); Werner D. Ducke, Greenwood (AU)

(73) Assignee: Cook Medical Technologies LLC, Bloomington, IN (US)

( * ) Notice: Subject to any disclaimer, the term of this patent is extended or adjusted under 35 U.S.C. 154(b) by 573 days.

(21) Appl. No.: 12/687,457

(22) Filed: Jan. 14, 2010

(65) Prior Publication Data

US 2010/0198328 A1    Aug. 5, 2010

(30) Foreign Application Priority Data

Feb. 2, 2009 (AU) .................................. 2009200350

(51) Int. Cl.
*A61F 2/06* (2013.01)

(52) U.S. Cl.
USPC ............................................ 623/1.11

(58) Field of Classification Search
USPC ................. 623/1.11–1.23; 606/108
See application file for complete search history.

(56) References Cited

U.S. PATENT DOCUMENTS

| | | | |
|---|---|---|---|
| 5,693,083 A | 12/1997 | Baker et al. | |
| 5,769,885 A | 6/1998 | Quiachon et al. | |
| 6,939,352 B2 * | 9/2005 | Buzzard et al. | 606/108 |
| 6,939,370 B2 * | 9/2005 | Hartley et al. | 623/1.11 |
| 7,611,529 B2 * | 11/2009 | Greenberg et al. | 623/1.11 |
| 7,763,063 B2 * | 7/2010 | Arbefeuille et al. | 623/1.11 |
| 7,803,177 B2 * | 9/2010 | Hartley et al. | 623/1.11 |
| 7,867,270 B2 * | 1/2011 | Hartley et al. | 623/1.11 |
| 7,892,275 B2 * | 2/2011 | Hartley et al. | 623/1.11 |
| 8,012,193 B2 * | 9/2011 | Hartley et al. | 623/1.11 |
| 8,043,354 B2 * | 10/2011 | Greenberg et al. | 623/1.12 |
| 8,114,145 B2 * | 2/2012 | Hartley et al. | 623/1.11 |
| 8,118,854 B2 * | 2/2012 | Bowe | 623/1.11 |
| 2002/0095204 A1 | 7/2002 | Thompson et al. | |
| 2004/0098079 A1 | 5/2004 | Hartley et al. | |
| 2007/0043425 A1 | 2/2007 | Hartley et al. | |

(Continued)

FOREIGN PATENT DOCUMENTS

| | | |
|---|---|---|
| WO | 2007142962 A2 | 12/2007 |
| WO | 2008/042270 A1 | 4/2008 |
| WO | 2009148602 A1 | 12/2009 |
| WO | PCTUS10020738 | 4/2010 |

OTHER PUBLICATIONS

Rasmussen et al for U.S. Appl. No. 61/130,952, filed Jun. 4, 2008.

*Primary Examiner* — Katherine Dowe
*Assistant Examiner* — Amy Shipley
(74) *Attorney, Agent, or Firm* — Richard J. Godlewski

(57) ABSTRACT

A multi-port stent graft delivery device (100) has an annular access lumen (107) between a delivery catheter (112) and a main sheath (106), at least one indwelling access sheath (118, 122) within the access lumen, and an indwelling guide wire (138, 146) within the or each access sheath and a stent graft (131) retained in the delivery device. Upon deployment of the stent graft into the vasculature of a patient the indwelling guide wire can be used to facilitate stabilisation of the access sheath during cathertisation of a side branch and deployment of a side arm covered or uncovered stent therein through the advanced access sheath. A two part handle enables withdrawal of a nose cone dilator before final placement of the side arm stents. A manifold (114) associated with a proximal handle portion provides a plurality of access ports (116, 120).

10 Claims, 6 Drawing Sheets

(56) References Cited

U.S. PATENT DOCUMENTS

| | | |
|---|---|---|
| 2007/0299499 A1 | 12/2007 | Hartley et al. |
| 2008/0033354 A1 | 2/2008 | Hartley et al. |
| 2008/0109065 A1 | 5/2008 | Bowe |
| 2009/0024137 A1 | 1/2009 | Chuter et al. |
| 2009/0171434 A1* | 7/2009 | Rusk et al. ............. 623/1.12 |
| 2009/0192518 A1* | 7/2009 | Golden et al. ............ 606/108 |
| 2011/0144735 A1* | 6/2011 | Hartley et al. ........... 623/1.11 |
| 2011/0307048 A1* | 12/2011 | Ivancev et al. ........... 623/1.11 |

* cited by examiner

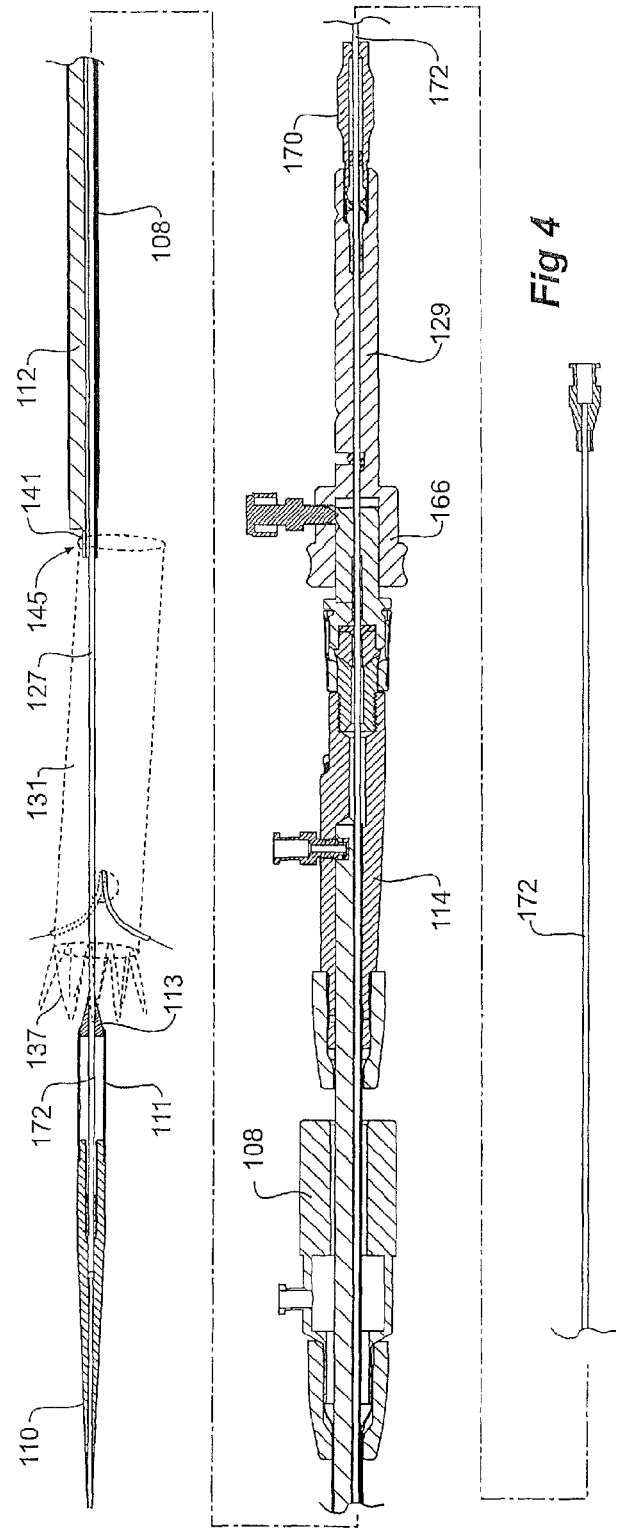
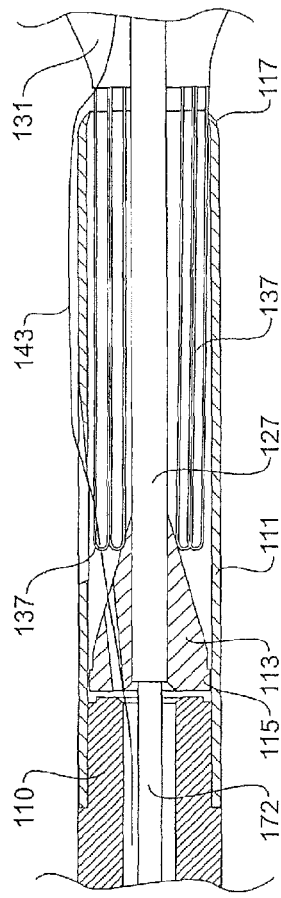
Fig 4
Fig 4A

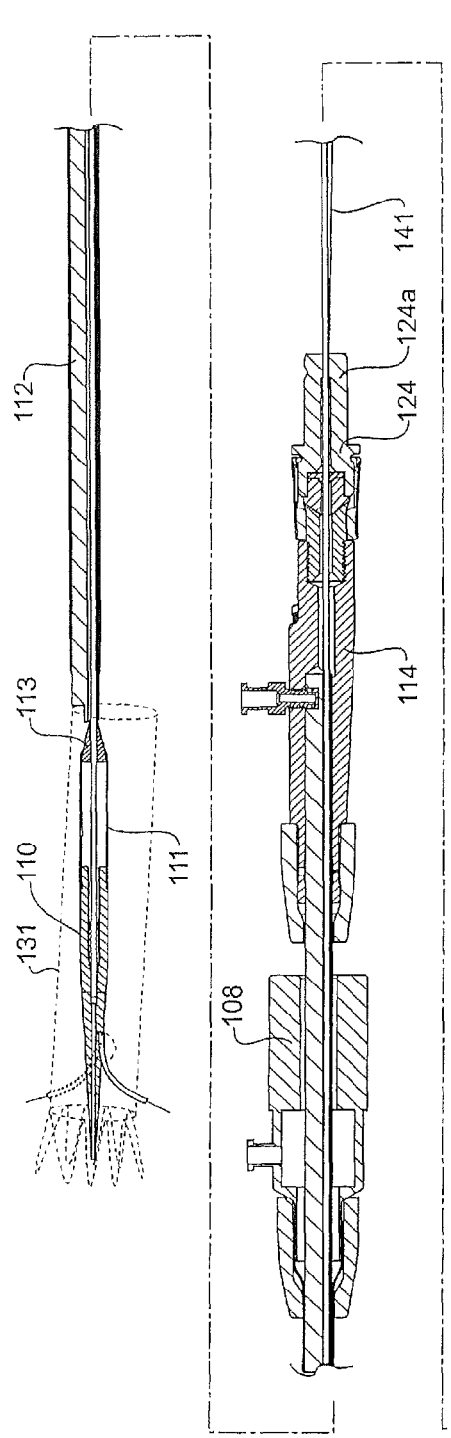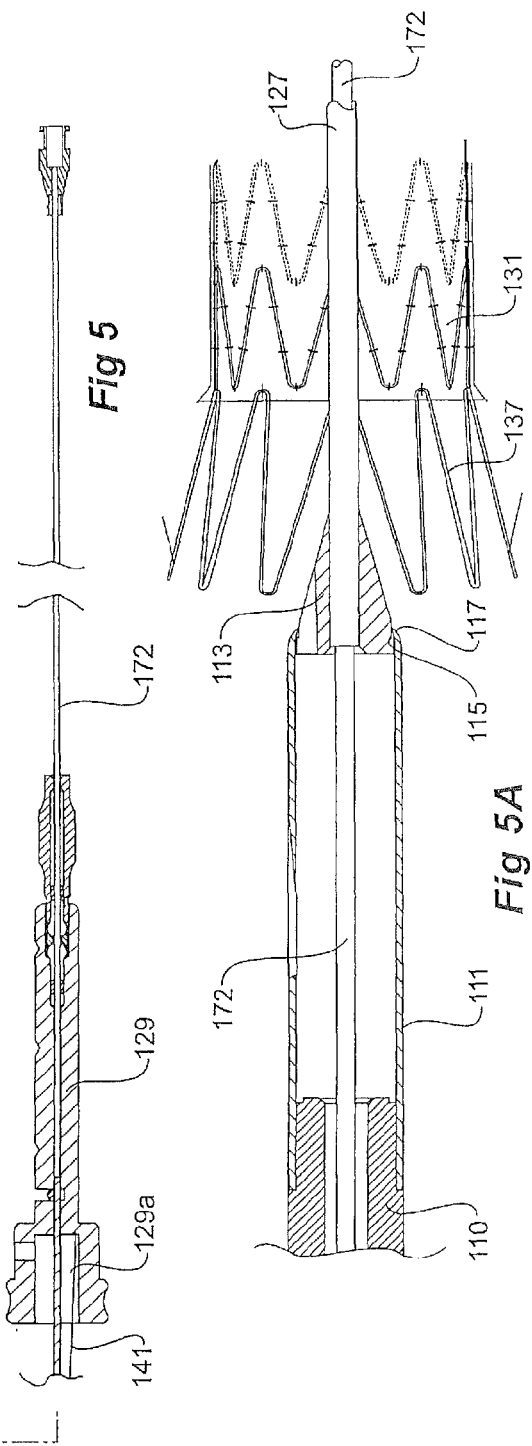
Fig 5
Fig 5A

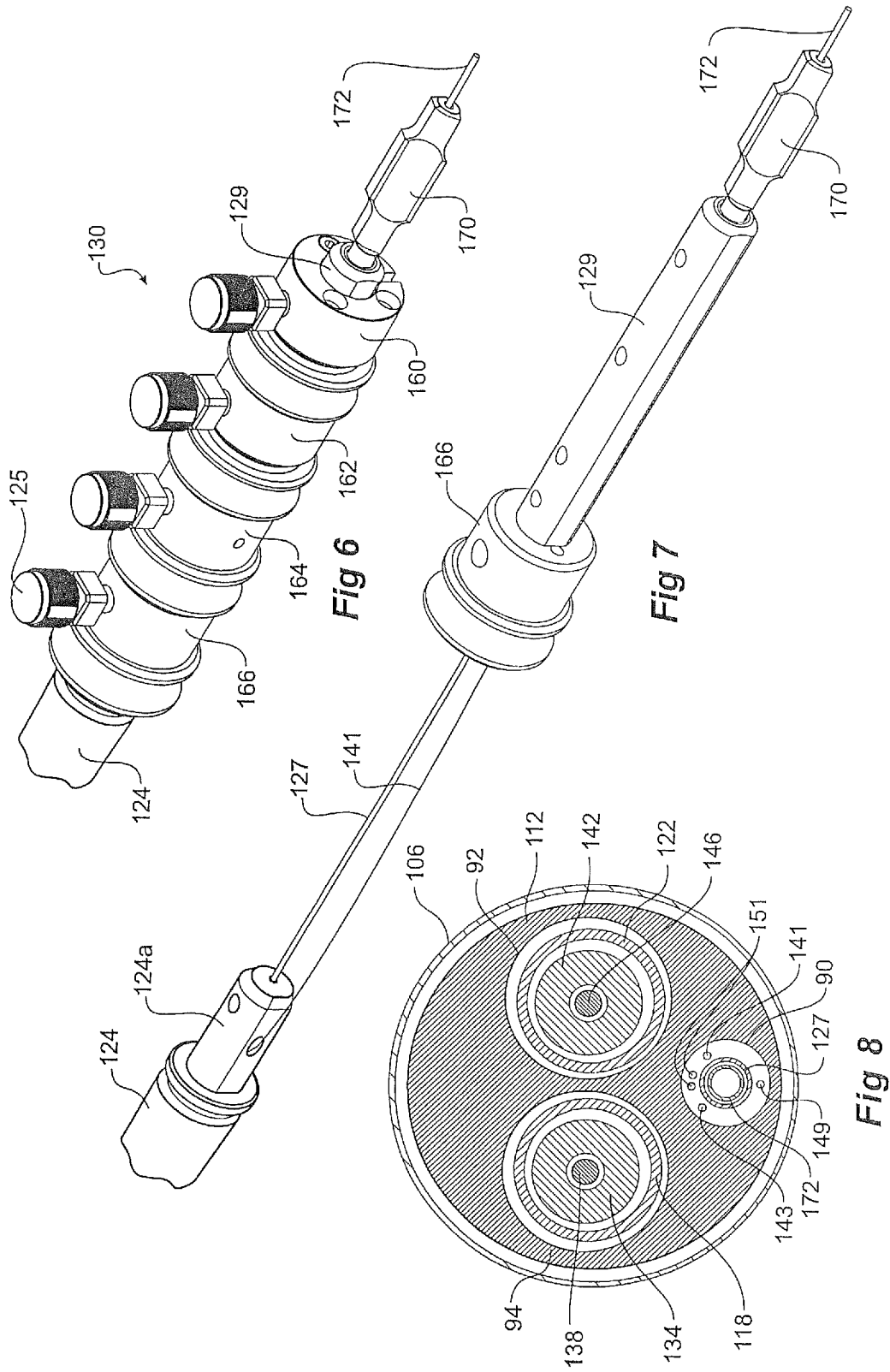

PRELOADED STENT GRAFT DELIVERY DEVICE

TECHNICAL FIELD

This invention relates to a medical device and more particularly to a device for introduction of stent grafts into the vasculature of a patient.

BACKGROUND OF THE INVENTION

It is known to introduce endovascular stent grafts into the vasculature of a patient to bridge an aneurism or damaged portion of the wall of the vasculature. Problems can occur, however, where the damage to the vasculature includes or is adjacent to a branch vessel from a main artery because occlusion of the branch vessel may cause permanent damage to the patient.

Examples of such branch vessels are the renal and the mesenteric arteries extending from the aorta.

Fenestrations in a stent graft have been proposed to allow access to the branch vessel from a main stent graft but it is often necessary to provide a side branch graft to maintain access into the branch vessel. Catheterisation of such a branch vessel from a delivery device through the fenestration enables deployment of a covered stent or uncovered stent into the side vessel. This invention provides an improved apparatus for catheterisation and deployment of side branch grafts.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

DESCRIPTION OF THE INVENTION

In one form, therefore, the invention is said to reside in a stent graft delivery device comprising a proximal delivery portion, a distal delivery portion and a handle assembly, the handle assembly comprising a proximal handle portion and a distal handle portion, the distal handle portion being movable longitudinally with respect to the proximal handle portion, a guide wire catheter extending through each of the distal handle portion and the proximal handle portion, the guide wire catheter being releasably affixed at a distal end to the distal handle portion and being affixed at a proximal end to the proximal delivery portion, the guide wire catheter the proximal delivery portion and the distal handle portion being movable longitudinally with respect to the proximal handle portion whereby the proximal delivery portion can be retracted independently of the distal delivery portion.

Preferably the proximal delivery portion comprises a nose cone dilator. The nose cone dilator can comprise a distally facing capsule fixed to the nose cone dilator and a proximal end of a stent graft being receivable in the capsule.

There can be further included a distal retrieval taper device in the capsule, the distal retrieval taper device being mounted onto the guide wire catheter and movable longitudinally with respect to the guide wire catheter, a distal retrieval catheter coaxially on the guide wire catheter and movable longitudinally with respect to the guide wire catheter, the distal retrieval catheter being fixed to the distal retrieval taper device at a proximal end and to the distal handle portion at a distal end whereby movement of the guide wire catheter with respect to the distal handle portion moves the distal retrieval taper device with respect to the distally opening capsule such that the distal retrieval taper device can move to a distal end of the capsule to extend from the capsule whereby to provide a smooth transition from the otherwise distal opening of the capsule to enable retraction of the nose cone dilator through a deployed stent graft.

Preferably the proximal handle portion is releasably fastened to the distal handle portion.

In an alternative form the invention is said to reside in a stent graft delivery device comprising;

a guide wire catheter having a guide wire lumen therethrough;

a handle at a distal end of the guide wire catheter, the handle including a plurality of access ports, the handle also including a proximal handle portion and a distal handle portion, the distal portion being movable with respect to the proximal portion; the guide wire catheter being movable longitudinally and rotationally with respect to both the proximal handle portion and the distal handle portion;

a nose cone dilator at the proximal end of the guide wire catheter;

a pusher catheter affixed to and extending from the proximal handle portion, the pusher catheter comprising a guide wire lumen and at least one auxiliary lumen, the guide wire catheter extending through the guide wire lumen;

a sheath arrangement extending from a sheath manipulator on the pusher catheter to the nose cone dilator, the sheath arrangement being coaxial with and surrounding the pusher catheter;

a stent graft on the guide wire catheter, distal of the nose cone dilator and proximal of the pusher catheter and within the sheath arrangement, the stent graft comprising a proximal end, a distal end, a peripheral wall defining a lumen therethrough and at least one fenestration in the peripheral wall;

the proximal end of the stent graft being releasably retained by a retention and release arrangement distally of the nose cone dilator; the retention and release arrangement distal of the nose cone dilator for the proximal end of the stent graft comprising a distally facing capsule fixed to the nose cone dilator and the proximal end of the stent graft being received in the capsule;

a distal retrieval taper device in the capsule, the distal retrieval taper device being mounted onto the guide wire catheter and movable longitudinally with respect to the guide wire catheter, a distal retrieval taper catheter coaxially on the guide wire catheter and movable longitudinally with respect to the guide wire catheter, the distal retrieval taper catheter being fixed to the distal retrieval taper device at a proximal end and to the distal handle portion at a distal end whereby movement of the guide wire catheter with respect to the distal handle portion moves the distal retrieval taper device with respect to the distally opening capsule such that the distal retrieval taper device can move to a distal end of the capsule to extend from the capsule whereby to provide a smooth transition from the otherwise distal opening of the capsule to enable retraction of the nose cone dilator through a deployed stent graft, an indwelling access sheath within the or each auxiliary lumen, the at least one indwelling access sheath extending from the handle and having a proximal end terminating distally of the stent graft;

an indwelling guide wire within the or each access sheath; the indwelling guide wire extending through the stent graft and exiting at the at least one fenestration and extending proximally within the sheath arrangement;

whereby upon deployment of the stent graft into the vasculature of a patient the indwelling guide wire can be used to facilitate cathertisation of a side branch or target vessel or be used to stabilise the access sheath during catheterisation, advancement of the access sheath into the target vessel and deployment of a covered or uncovered stent therein through the access sheath and whereby the proximal nose cone dilator can be retracted independently of the pusher catheter.

Preferably there is a dilator extending through the or each access sheath and comprising a dilator tip at the proximal end of the or each access sheaths, the dilator being able to be withdrawn through the access sheath.

The stent graft preferably comprises a proximal exposed stent, the proximal exposed stent being received in the capsule and whereby the proximal exposed stent is released by advancement of the nose cone dilator.

The retention and release arrangement distal of the nose cone dilator for the proximal end of the stent graft preferably comprises a first trigger wire system engaging the stent graft or a stent of the stent graft within the nose cone dilator and a first release arrangement on the distal handle portion for the first trigger wire.

The stent graft preferably includes diameter reducing ties and the delivery device further includes a second release arrangement on the distal handle portion for the diameter reducing ties.

Preferably the second release arrangement for the diameter reducing ties comprises a second release arrangement on the distal handle portion and a release wire extending from the second release arrangement on the distal handle portion to the diameter reducing ties.

There may be further included a retention arrangement for the distal end of the stent graft comprising a tie arrangement engaging the stent graft, a third release grip on the handle and at least one trigger wire extending from the third release grip to the tie arrangement.

Preferably the proximal handle portion comprises a haemostatic seal assembly for the or each access sheath and the or each access sheath extends through the respective haemostatic seal assembly.

Preferably the indwelling guide wire extends through the access sheath and the stent graft and exits at the least one fenestration and extends proximally within the main sheath and is releasably fastened to the peripheral wall of the stent graft proximally of the fenestration to stabilise the indwelling guide wire during advancement of the dilator and access sheath and catheterisation of the branch vessel.

Preferably the releasable fastening comprises a release wire stitched in to peripheral wall of the stent graft proximally of the fenestration, an engagement protrusion of the indwelling guide wire and a suture engaged around the release wire and the indwelling guide wire distally of the engagement protrusion whereby upon retraction of the release wire the suture is released from engagement with the indwelling guide wire.

Preferably the proximal handle portion is releasably fastened to the distal handle portion.

It will be seen that by the various embodiments of the invention there is provided a device where the main delivery catheter and the sheaths for each of the side branch catheterisation devices are included within the main sheath of the stent graft with each of the components being able to be manipulated separately. During deployment and before final placement of the covered or uncovered side branch stents the nose cone dilator can be retracted to distal of the fenestrations by movement of the distal handle portion.

This then generally describes the invention but to assist with understanding reference will now be made the accompanying drawings which show preferred embodiments of the invention.

BRIEF DESCRIPTION OF THE DRAWING

In the drawings:

FIG. 4 shows the embodiment shown in FIG. 3 in a first partially activated condition;

FIG. 4A shows the embodiment shown in FIG. 3 and in particular a detail of a part of the nose cone dilator and capsule with the distal retrieval taper;

FIG. 5 shows the embodiment shown in FIG. 3 in a second partially activated condition;

FIG. 5A shows the embodiment shown in FIG. 3 and in particular a detail of a part of the nose cone dilator and capsule with the distal retrieval taper in its distal position;

FIG. 6 shows a perspective view of part of the handle of the embodiment shown in FIG. 3;

FIG. 7 shows the view of FIG. 6 in a activated condition; and

FIGS. 8 shows a transverse cross sectional view of the pusher catheter portion of the embodiment shown in FIG. 1 along the line 8-8'.

DETAILED DESCRIPTION

Figure 1:
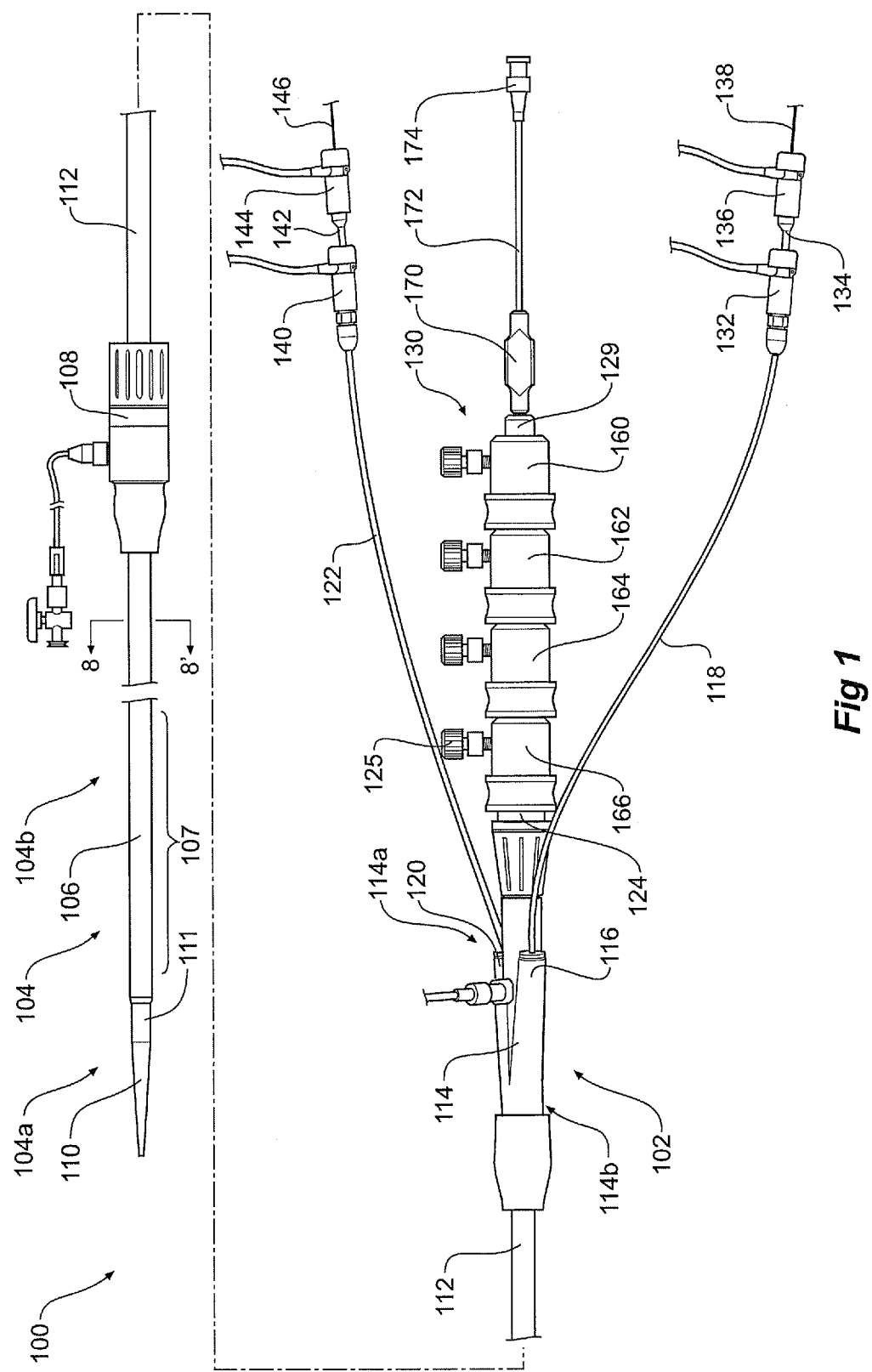
FIG. 1 shows a first embodiment of stent graft introducer incorporating the split handle of the present invention.

The drawings show a first embodiment of multi port stent graft introducer incorporating a split handle arrangement according to the present invention.

The introducer device 100 comprises a handle and manifold assembly 102 and introduction portion 104 intended to be deployed into the patient by the known Seldinger method. The introduction portion 104 generally comprises a proximal delivery portion 104a and a distal delivery portion 104b. More specifically the introduction section 104 includes a sheath 106 extending from an sheath manipulator 108 to a nose cone dilator 110. A stent graft is retained within the outer sheath 106 in the region 107 just distal of the nose cone dilator 110.

The sheath manipulator 108 is positioned over a pusher catheter 112 which extends from a manifold 114. The manifold 114 has a proximal end 114b to which is affixed the pusher catheter 112 and two access ports 116, 120 at its distal end 114a. Access port 116 is for a first access sheath 118. Access port 120 is for a second access sheath 122. At the rear end 114a of the manifold a handle assembly 130 is connected. The handle assembly 130 includes trigger wire release mechanisms and can be separated into two parts is as discussed below.

The access sheath 118 extends to a haemostatic seal 132 through which extends a dilator 134. On the dilator 134 is a dilator haemostatic seal 136 through which extends an indwelling guide wire 138.

The access sheath 122 extends to a haemostatic seal 140 through which extends a dilator 142. On the dilator 142 is a dilator haemostatic seal 144 through which extends an indwelling guide wire 146.

The handle assembly 130 includes a proximal handle portion 124 which is affixed to the rear of the manifold 114. The handle assembly 130 also includes a distal handle portion 129. The distal handle portion 129 has a proximal recess 129a which fits over a distal extension 124a of the proximal handle portion 124 and a locking screw 125 releasably locks the two handle portions together.

The distal handle portion 129 of the handle assembly 130 includes trigger wire release mechanisms releasably mounted onto it from its distal end as follows. Trigger wire release 160 is for the release of the stabilisation retention of indwelling guide wires, trigger wire release 162 is for diameter reducing ties, trigger wire release 164 is for a retention trigger wire for the exposed stent in the capsule. Trigger wire release mechanism 166 is for the distal end of the graft. Trigger wire release mechanism 166 is also part of the distal portion of the handle 129.

U.S. patent application Ser. No. 11/507,115, filed Aug. 18, 2006 entitled "Assembly of Stent Grafts" teaches the use of diameter reducing ties for stent grafts and the teachings therein are incorporated herein in its entirety.

A pin vice 170 is at the rear of the handle assembly 130 and the guide wire catheter 172 for the introducer device extends through the pin vice 170 and is locked and can be released for movement with respect to the distal portion of the handle 130 by the pin vice. The guide wire catheter 172 terminates in a syringe point 174 to enable flushing liquid and radiopaque medium to be deployed through the delivery device.

The introduction portion 104 of the stent graft delivery device 100 has the nose cone dilator 110 and at the distal end of the nose cone dilator 110 is a distally opening capsule 111 for the receipt of an exposed stent 137 of a stent graft 131. The capsule 111 has a slightly in-turned distal end 117. This has two purposes, a first is to assist with engagement of the sheath 106 of the delivery device when the sheath is advanced to the nose cone dilator 110 and a second is to prevent complete withdrawal of a distal retrieval taper device 113 from the capsule as will be discussed below. The delivery device has a guide wire catheter 172 which passes through and is fastened to the nose cone dilator 110 at its proximal end and passes through a handle assembly 130 of the delivery device. The pin vice arrangement 170 at the distal end of the distal handle portion 129 locks movement of the guide wire catheter 172 with respect to the distal portion of the handle 129 and can be loosened to allow relative motion between these components as discussed below. Within the capsule 111 is the distal retrieval taper device 113.

Figure 2:
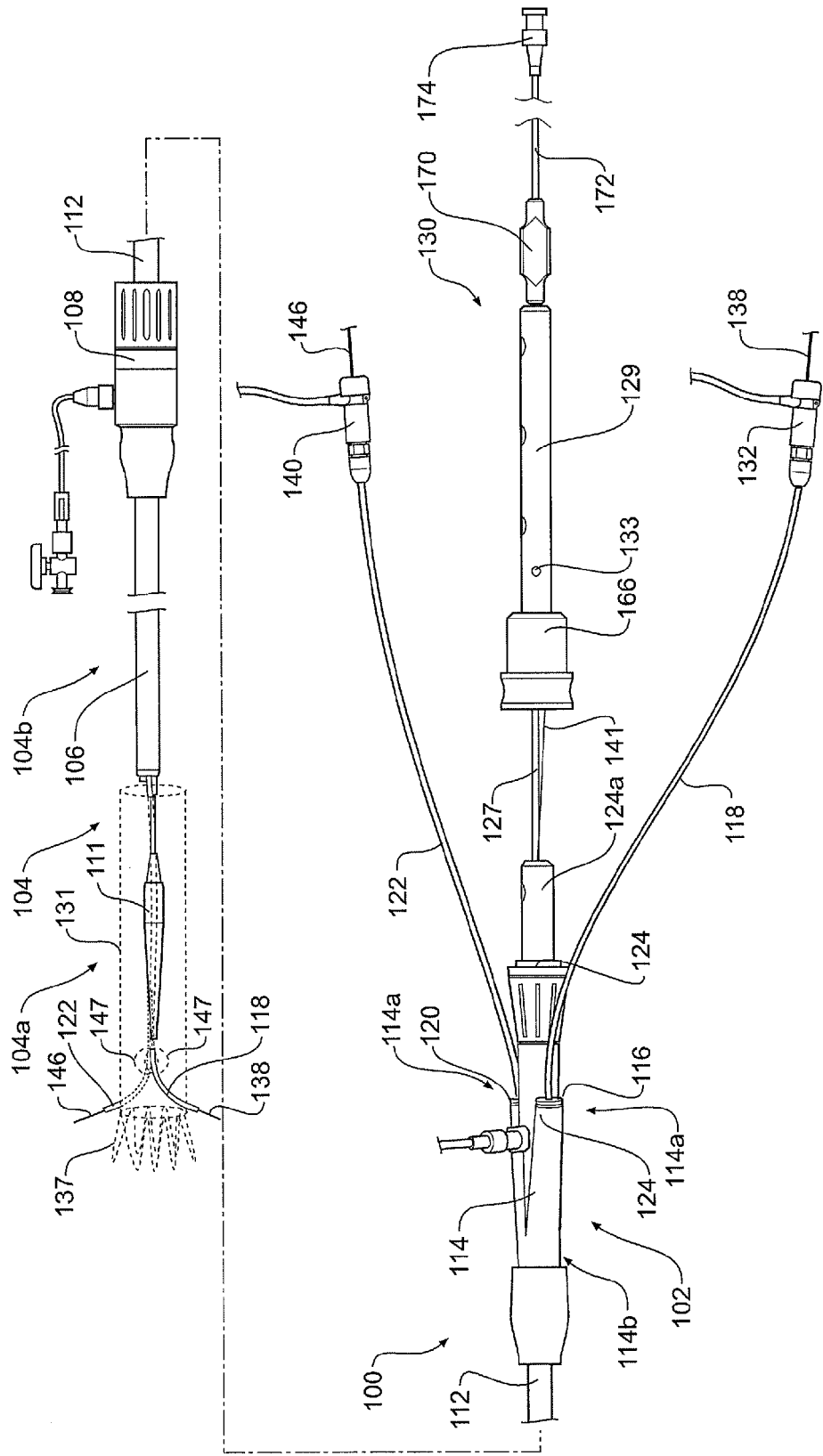
FIG. 2 shows the embodiment shown in FIG. 1 in a partially activated condition.

The stent graft 131 shown in FIG. 2 for instance comprises a tubular body of a biocompatible graft material such as Dacron, expanded PTFE or Thoralon, a polyurethane material. The stent graft is supported by self expanding stent (not shown for clarity). A proximally extending exposed stent 137 assist with providing infra-renal fixation of the deployed stent graft. The stent graft has two fenestration 147 which are provided to give access to the renal arteries. The stent graft is retained on the delivery device by proximal retention of the exposed stent 137 into the capsule 111 of the delivery device and distally by a trigger wire retention 145. Diameter reducing ties can be used to hold the stent graft in a diameter reduced condition during the initial catheterisation of a side branch because it may still be necessary to move the stent graft proximally or distally or rotate it. In the diameter reduced condition this is still possible whereas when released to full diameter this may not be possible.

Figures 3, 3A:
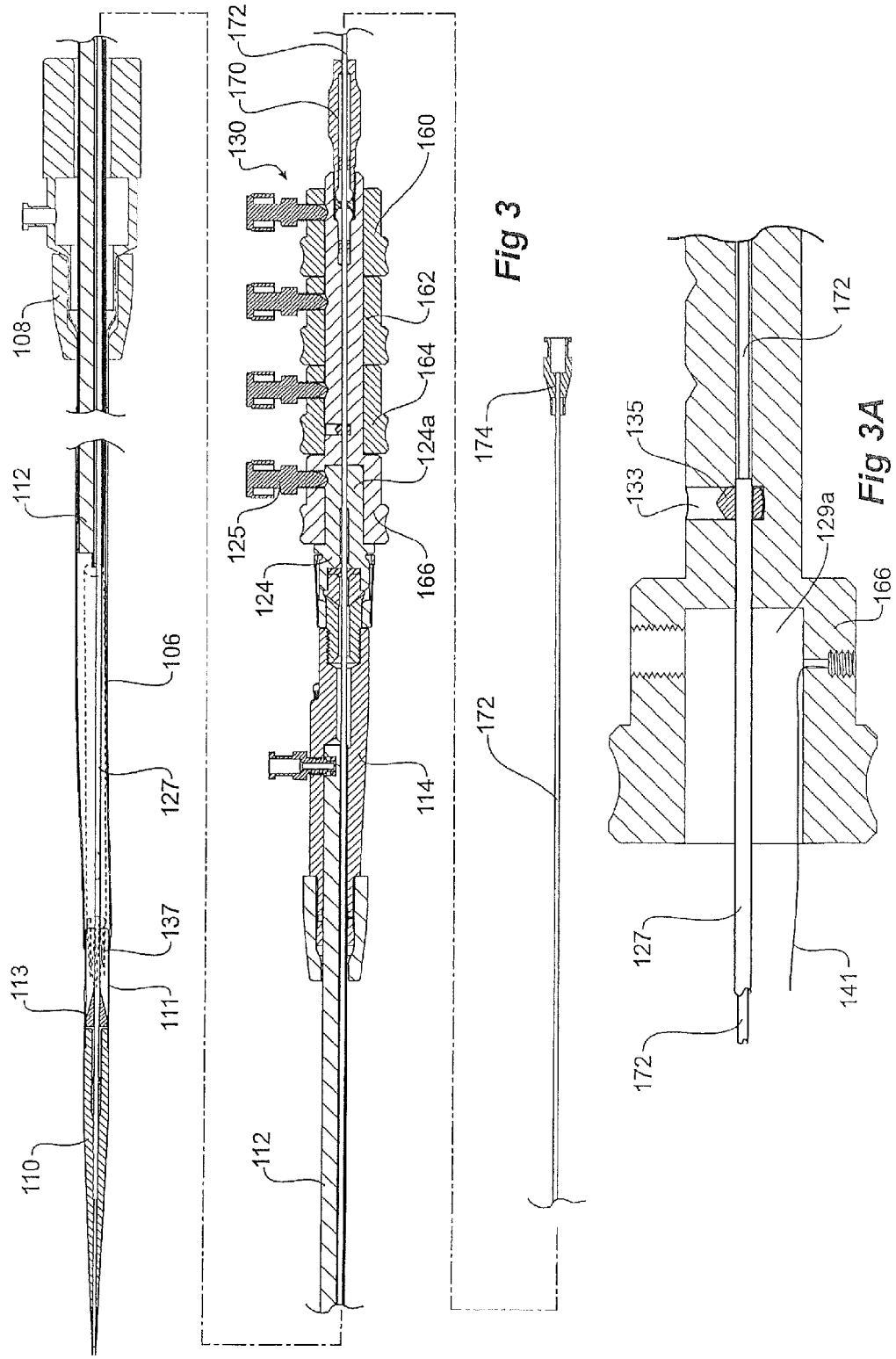
FIG. 3 shows a longitudinal cross sectional view of the embodiment of a stent graft introducer of FIG. 1 according the present invention.
FIG. 3A shows the embodiment shown in FIG. 3 and in particular a detail of a part of the distal handle portion.

As can be seen particularly in FIG. 4A and 5A the distal retrieval taper device fits coaxially around the guide wire catheter 172 and can move longitudinally along the guide wire catheter. A retrieval catheter 127 is mounted coaxially around the guide wire catheter 172 and can move longitudinally along the guide wire catheter. At its proximal end the retrieval catheter 127 is joined to the distal retrieval taper device 113 and at its distal end the retrieval catheter 127 is joined to the distal handle portion 129 at 133 by a suitable adhesive 135. For this purpose apertures are provided into the handle and adhesive is applied through these apertures. FIG. 3A shows detail of the mounting of the retrieval catheter into the distal handle portion.

The distal retrieval taper device is shown in detail in FIGS. 4A and 5A. The distal retrieval taper device 113 has an enlarged shoulder 115 at its proximal end. The shoulder is sized so that it is of greater diameter than the smallest part of the in-turned distal end 117 of the capsule 111. By this arrangement the distal retrieval taper device can move through the capsule but cannot be fully removed from the capsule. The retrieval catheter 127 is coaxial with the guide wire catheter 172. At its proximal end the retrieval catheter 127 is affixed to the distal retrieval taper device and at its proximal end the retrieval catheter 127 is affixed to the distal handle portion 129 as shown in FIG. 3A. This means that movement of the guide wire catheter 172 proximally with respect to the distal handle portion 129, after release of the pin vice 170 will move the nose cone dilator 110 and capsule 111 with respect to the distal retrieval taper device with the effect that the distal retrieval taper extends from the capsule thereby providing a smooth tapered surface for retrieval of the nose cone dilator through the stent graft. Locking of the pin vice after the distal retrieval taper 113 has been moved to the distal end of the capsule 111 ensures that all of the distal retrieval taper, the capsule, the nose cone dilator and the distal handle portion all move together.

U.S. Provisional Patent Application Ser. No. 61/130,952, filed Jun. 4, 08 and entitled "Top Cap Retrieval Arrangement" teaches distal retrieval taper devices (referred to therein as tapered plugs) and the teaching therein is incorporated herein in its entirety.

By this arrangement the nose cone dilator can be moved to a distal position with respect to fenestrations in the stent graft so that the nose cone dilator does not interfere with the deployment of side branch covered or uncovered stent grafts through such fenestrations nor does any subsequent retraction of the nose cone dilator interfere with the deployed of side branch side branch covered or uncovered stent grafts.

U.S. patent application Ser. No. 11/904,834, filed Sep. 28, 07 entitled "Endovascular Delivery Device" teaches apparatus and methods of deployment of stent grafts and side branch stent graft into fenestration of such stent grafts and the teaching therein is incorporated herein in its entirety. The use of the stabilisation retention of the indwelling guide wire is particularly discussed therein.

As can be seen particularly in FIG. 8, which is a transverse cross section along the line 8-8' as shown in FIG. 1, the pusher catheter 112 is surrounded by the sheath 106. The pusher catheter has three longitudinally extending lumens. A first lumen is the guide wire lumen 90 and this lumen is off-set from the centre of the pusher catheter to allow for two auxiliary lumens 92 and 94. The guide wire lumen 90 has passing through it the guide wire catheter 172 and coaxially around that the retrieval catheter 127. Also in the guide wire lumen are the trigger wires for the diameter reducing ties 149, the top capsule 143, the distal retention 141 and the auxiliary guide wire stabilisation 151. The auxiliary lumen 94 has the access sheath 118 extending through it and the dilator 134 and guide wire 138 extend through the access sheath 118. The auxiliary lumen 92 has the access sheath 122 extending through it and the dilator 142 and guide wire 146 extend through the access sheath 122.

A process for use of the delivery device of the embodiment of the invention shown herein is as follows.

In this embodiment the deployment device has the following components:

i) Guide wire catheter 172 extending from a handle 130 to a nose cone dilator 110.
ii) Handle 130 comprises a proximal handle portion 124 and a distal handle portion 129.
   (a) Trigger wire releases for top cap 164, diameter reducing ties 162 and stabilisation retention of indwelling guide wire 160 on the distal portion of handle with respective trigger wires. Only the trigger wire 143 for the top cap retention of the exposed stent is shown, see FIG. 4A.
   (b) Trigger wire releases for distal end on proximal portion with respective trigger wire 141, see FIGS. 2, 3A and 7.
iii) Pusher catheter 112 with lumens for access sheath 92, 94 and guide wire catheter 90 joined to proximal handle portion 124 vial manifold 114.
iv) Sheath 106 with sheath manipulator 108 on pusher 112.
v) Nose cone dilator 110 with a distally opening top capsule 111.
vi) Indwelling guide wires 138, 146 through fenestrations 147 in stent graft 131 and into top capsule 111. Indwelling guide wires go through access sheaths 118, 122.
vii) Stabilisation retention of indwelling guide wires 138 and 146 proximally of fenestration (not shown).
viii) Distal retrieval taper 113 in top capsule 111 coaxial with guide wire catheter 172 and a retrieval cannula 127 extending from retrieval taper 113 to and fixed to distal portion of handle 129.
ix) Each access sheath 118, 122 has a dilator 134, 142 within it extending to a dilator tip (not shown);
x) Stent graft 131 with
   (i) proximally extending exposed stent 137 received in top capsule 111 and a top cap trigger wire 143 retention
   (ii) distal retention at 145
   (iii) Fenestrations for renal arteries, for instance 147
   (iv) radiopaque markers (not shown)
   (v) diameter reducing ties (not shown)

Introduction steps are as follows:

(a) Position the introduction part 104 of the deployment device 100 into the aorta correctly taking into account N-S position as well as rotational position with respect to target vessels and fenestrations on the stent graft 131 using markers on stent graft body. At this stage the deployment device is s as shown in FIGS. 1 and 3.

(b) Withdraw the outer sheath 106 of the deployment device while continuing to check position until the distal end of the stent graft opens. At this stage the distal end of the stent graft is still retained by distal fixation, the proximal end is retained by the exposed stent retained in top capsule of the deployment device and the expansion of the stent graft is restricted by the diameter reducing ties. This stage is shown in part in FIG. 4A.

(c) Advance the access sheaths 118, 122 (left and right) on their respective indwelling guide wires 138 146 through the lumen of stent graft 131 to or through the fenestration 147 (at this stage the top capsule still retains the exposed stent and the indwelling guide wires).

(d) Position the access sheath at the opening of the fenestration.

(e) Remove the dilator 134, 142 of the access sheath.

(f) Advance an additional catheter and additional guide wire (4-5 Fr) through the access sheath and into the target vessel. The additional catheter may have a crooked or hockey stick tip to facilitate access.

(g) Remove the guide wire from the additional catheter and re-insert a stiffer wire into the target vessel (eg renal artery).

(h) Release the stabilisation retention of indwelling guide wire (i) Retrieve the indwelling wire guide from the top cap and pull it out completely.

(j) Remove the additional catheter and replace the access sheath dilator and dilator catheter over the stiffer wire in the target vessel and advance the access sheath over the stiffer wire into the target vessel. Withdraw the access sheath dilator.

(k) Repeat steps (d) to (j) for the other of the target vessels.

(l) Advance covered stents through the access sheaths into the target vessels but do not release.

(m) Release the diameter reducing ties by releasing and withdrawing trigger wire release 160.

(n) Release the top capsule 111 by removing the locking trigger wire 143 via trigger wire release 162, releasing the pin vice 170 and advancing the top capsule on the guide wire catheter and release the top exposed stent. At the same time the distal retrieval taper moves from the proximal end of the capsule to the distal end of the capsule. This stage is shown in FIG. 4.

(o) Tighten the pin vice 170.

(p) Retract the nose cone dilator, top cap and distal retrieval taper past the fenestration by removing the locking screw of the distal handle portion and retracting distal portion of handle. This also releases the distal attachment via trigger wire 141 connected to trigger wire release 166. This stage is shown in FIGS. 2 and 5.

(q) One at a time, withdraw the access sheaths from the target vessels and deploy covered stents between the fenestrations and target vessels and balloon expand if necessary including flaring within the main stent graft.

(r) Remove both access sheaths and also the guide wires from the target vessels and withdraw them from the system.

(s) Retract the nose cone dilator, top cap and distal retrieval taper to the sheath 106.

(t) Withdraw the entire assembly or leave the outer sheath in place for further deployments. Further deployment may include a bifurcated distal component.

It is seen that by this invention an arrangement is provided that by which access sheaths may extend through the introduction device and are able to be separately manipulated to enable access to renal or other arteries within the vasculature of a patient.

What is claimed is:

1. A stent graft delivery device comprising a proximal delivery portion, a distal delivery portion and a handle assembly, the handle assembly comprising a proximal handle portion and a distal handle portion, the distal handle portion being movable longitudinally with respect to the proximal handle portion, a guide wire catheter extending through each of the distal handle portion, the proximal handle portion, and the distal delivery portion, the guide wire catheter being releasably affixed at a distal end thereof to the distal handle portion by a locking device and being affixed at a proximal end thereof to the proximal delivery portion;

the guide wire catheter, the proximal delivery portion, and the distal handle portion being movable longitudinally with respect to the proximal handle portion whereby the proximal delivery portion can be retracted independently of the distal delivery portion;

a sheath arrangement comprising a sheath, the sheath arrangement being mounted onto the distal delivery portion and movable longitudinally with respect to the distal handle portion and the sheath extending proximally to the proximal delivery portion;

the proximal delivery portion comprising a nose cone dilator, a distally facing capsule fixed to the nose cone dilator, a distal retrieval taper device in the capsule, the distal retrieval taper device being mounted onto the guide wire catheter and movable longitudinally with respect to the guide wire catheter, a distal retrieval catheter coaxially on the guide wire catheter and movable longitudinally with respect to the guide wire catheter, the distal retrieval catheter being fixed to the distal retrieval taper device at a proximal end and to the distal handle portion at a distal end whereby movement of the guide wire catheter with respect to the distal handle portion moves the distal retrieval taper device with respect to the distally opening capsule such that the distal retrieval taper device can move to a distal end of the capsule to extend from the capsule whereby to provide a smooth transition from the otherwise distal opening of the capsule to enable retraction of the nose cone dilator;

a trigger wire situated at least partially outside the capsule, extending into the capsule via an aperture in the capsule wall, and further extending into the nose cone dilator via an aperture in the distal taper device.

2. A stent graft delivery device as in claim 1 wherein the proximal handle portion is releasably fastened to the distal handle portion.

3. A stent graft delivery device as in claim 1 wherein the proximal handle portion comprises a plurality of access ports;

the distal delivery portion comprises a pusher catheter affixed to and extending from the proximal handle portion, the pusher catheter comprising a guide wire lumen and at least one auxiliary lumen, the guide wire catheter extending through the guide wire lumen;

a stent graft on the guide wire catheter-distal of the nose cone dilator and proximal of the pusher catheter and within the sheath arrangement, the stent graft comprising a proximal end, a distal end, having a peripheral wall defining a lumen therethrough and at least one fenestration in the peripheral wall;

an indwelling access sheath within the or each auxiliary lumen, the at least one indwelling access sheath extending from the proximal handle portion and having a proximal end terminating distally of the stent graft;

an indwelling guide wire within the or each access sheath;

the indwelling guide wire extending through the stent graft and exiting the at least one fenestration and extending proximally within the sheath arrangement;

whereby upon deployment of the stent graft into the vasculature of a patient the indwelling guide wire can be used to facilitate catheterisation of a side branch or target vessel or be used to stabilise the access sheath during catheterisation, advancement of the access sheath into the target vessel and deployment of a covered or uncovered stent therein through the access sheath and whereby the nose cone dilator can be retracted independently of the pusher catheter.

4. A stent graft delivery device as in claim 1 wherein the locking device comprises a pin vice.

5. A stent graft delivery device comprising a proximal delivery portion, a distal delivery portion and a handle assembly, the proximal delivery portion comprising a nose cone dilator and the distal delivery portion comprising a pusher catheter, the handle assembly comprising a proximal handle portion and a distal handle portion, the distal handle portion being movable longitudinally with respect to the proximal handle portion;

a guide wire catheter extending through each of the distal handle portion, the proximal handle portion and the pusher catheter, the guide wire catheter being releasably affixed at a distal end thereof to the distal handle portion by a pin vice and being affixed at a proximal end thereof to the nose cone dilator, the guide wire catheter, the proximal delivery portion and the distal handle portion being movable longitudinally with respect to the proximal handle portion whereby the nose cone dilator can be retracted independently of the distal delivery portion;

a sheath arrangement comprising a sheath, the sheath arrangement being mounted onto the pusher catheter and movable longitudinally with respect to the pusher catheter and the sheath extending proximally to the nose cone dilator;

the nose cone dilator comprising a distally facing capsule fixed to the nose cone dilator, a distal retrieval taper device in the capsule, the distal retrieval taper device being mounted onto the guide wire catheter and movable longitudinally with respect to the guide wire catheter, a distal retrieval catheter coaxially on the guide wire catheter and movable longitudinally with respect to the guide wire catheter, the distal retrieval catheter being fixed to the distal retrieval taper device at a proximal end and to the distal handle portion at a distal end whereby movement of the guide wire catheter with respect to the distal handle portion moves the distal retrieval taper device with respect to the distally opening capsule such that the distal retrieval taper device can move to a distal end of the capsule to extend from the capsule whereby to provide a smooth transition from the otherwise distal opening of the capsule to enable retraction of the nose cone dilator;

the proximal handle portion comprising a plurality of access ports, the pusher catheter comprising a guide wire lumen and at least one auxiliary lumen, the guide wire catheter extending through the guide wire lumen;

a stent graft on the guide wire catheter distal of the nose cone dilator and proximal of the pusher catheter and within the sheath arrangement, the stent graft comprising a proximal end, a distal end, a peripheral wall defining a lumen therethrough and at least one fenestration in the peripheral wall;

a retention and release arrangement distal of the nose cone dilator; releasably restraining the proximal end of the stent graft and comprising the distally facing capsule fixed to the nose cone dilator and the proximal end of the stent graft being received in the capsule;

a trigger wire system engaging the proximal end of the stent graft, a trigger wire situated at least partially outside the capsule, extending into the capsule via an aperture in the capsule wall, and further extending into the nose cone dilator via an aperture in the distal taper device;

an indwelling access sheath within the or each auxiliary lumen, the at least one indwelling access sheath extending from the proximal handle portion and having a proximal end terminating distally of the stent graft;

an indwelling guide wire within the or each access sheath;

the indwelling guide wire extending through the stent graft and exiting the at least one fenestration and extending proximally within the sheath arrangement;

whereby upon deployment of the stent graft into the vasculature of a patient the indwelling guide wire can be used to facilitate cathertisation of a side branch or target vessel or be used to stabilise the access sheath during catheterisation, advancement of the access sheath into the target vessel and deployment of a covered or uncovered stent therein through the access sheath and whereby the nose cone dilator can be retracted independently of the pusher catheter.

6. A delivery device comprising an introduction portion located at the proximal end of the delivery device, a pusher catheter located distal to the introduction portion and affixed to the proximal end of a manifold, a proximal handle portion attached to the distal end of the manifold, a distal handle portion releasably affixed to the distal end of the proximal handle portion, and at least one trigger wire mechanism releasably affixed to the distal handle portion;

the introduction portion comprising a nose cone dilator and a distally opening capsule, the distally opening capsule attached to the distal end of the nose cone dilator and containing a distal taper device;

a trigger wire situated at least partially outside the capsule, extending into the capsule via an aperture in the capsule wall, and further extending into the nose cone dilator via an aperture in the distal taper device;

a guidewire catheter extending through each of the distal handle portion, proximal handle portion, the manifold, the pusher catheter, the distal retrieval taper device, and being affixed at a proximal end thereof to the nose cone dilator and releasably affixed at a distal end thereof to the distal handle portion by a locking device;

a retrieval catheter being mounted coaxial with the guidewire catheter and affixed to the distal retrieval taper device at a proximal end and to the distal handle portion at a distal end;

the locking device being releasably affixed to the distal handle portion and the distal end of the guidewire catheter;

the pusher catheter comprising a guidewire lumen, the guidewire lumen completely enclosing a guidewire catheter, and at least one auxiliary lumen, each auxiliary lumen completely enclosing an access sheath;

each access sheath exiting the manifold through an access port.

7. The stent delivery device of claim 6 wherein the capsule has an slightly inward turned distal end, and the distal retrieval taper device having a proximal shoulder slightly larger than the smallest part of the slightly turned inward distal end.

8. The stent delivery device of claim 6 wherein the distal retrieval taper device has a smooth tapered surface.

9. The stent delivery device of claim 6 wherein the locking device comprises a pin vice.

10. The stent delivery device of claim 6 wherein the trigger wire mechanisms includes trigger wire release mechanisms for stabilisation retention of indwelling guide wires, a stent diameter reducing tie, for retention of the exposed stent in the capsule, and a for the distal end of the stent graft.

* * * * *